(12) United States Patent
Lee

(10) Patent No.: US 9,617,545 B2
(45) Date of Patent: Apr. 11, 2017

(54) METHOD FOR TREATING BREAST CANCER BY TARGETING BREAST CANCER STEM CELL

(71) Applicant: KYUNGPOOK NATIONAL UNIVERSITY INDUSTRY-ACADEMIC COOPERATION FOUNDATION, Daegu (KR)

(72) Inventor: You-Mie Lee, Daegu (KR)

(73) Assignee: Kyungpook National University Industry—Academic Cooperation Foundation (KR)

( * ) Notice: Subject to any disclaimer, the term of this patent is extended or adjusted under 35 U.S.C. 154(b) by 0 days.

(21) Appl. No.: 14/602,588

(22) Filed: Jan. 22, 2015

(65) Prior Publication Data

US 2016/0060634 A1   Mar. 3, 2016

(30) Foreign Application Priority Data

Aug. 28, 2014  (KR) ........................ 10-2014-0113554

(51) Int. Cl.
| | |
|---|---|
| *A61K 48/00* | (2006.01) |
| *C07H 21/02* | (2006.01) |
| *C07H 21/04* | (2006.01) |
| *C12N 15/85* | (2006.01) |
| *C12N 15/113* | (2010.01) |

(52) U.S. Cl.
CPC ........ *C12N 15/1137* (2013.01); *C12N 15/113* (2013.01); *C12N 15/1138* (2013.01); *C12Y 101/01027* (2013.01); *C12N 2310/14* (2013.01)

(58) Field of Classification Search
CPC .... C12N 15/113; C12N 2310/11; A61K 48/00
See application file for complete search history.

(56) References Cited

FOREIGN PATENT DOCUMENTS

WO    2008/110624 A2    9/2008

OTHER PUBLICATIONS

McCleland et al., "An Integrated Genomic Screen Identifies LDHB as an Essential Gene for Triple-Negative Breast Cancer", Cancer Res; 72(22); 5812-5823 (Nov. 8, 2012).
Kim et al., "Identification of Genes with Differential Expression in Doxorubicin-resistant Human Breast Cancer Cells using cDNA Microarray Analysis," Molecule & Cell Biology Society Winter Symposium-Poster Presentation, p. 116, KSMCB Winter Conference 2014.
Hasegawa et al., 2008, "CD109 expression in basal-like breast carcinoma", Pathology International, vol. 58; pp. 288-294.
Zha et al., 2011, "Lactate Dehydrogenase B is Critical for Hyperactive mTOR-Mediated Tumorigenesis", Cancer Res., vol. 71(1); pp. 13-18.

*Primary Examiner* — Amy Bowman
(74) *Attorney, Agent, or Firm* — Riverside Law LLP

(57) ABSTRACT

The present invention relates to a composition for inhibiting growth of cancer stem cells, which includes an EXT1, LDHB, CD109, EFEMP2, RASIP1 or SERPINE1 gene expression inhibitor as an active ingredient, and a method of treating cancer using the same. The composition has targeted therapeutic activities against cancer stem cells important for resistance, metastasis and recurrence of breast cancer, and thus can be useful in fundamentally treating, preventing or alleviating cancer such as breast cancer by directly inhibiting expression of EXT1, LDHB, CD109, EFEMP2, RASIP1 or SERPINE1 which are very important for growth of the cancer stem cells.

2 Claims, 14 Drawing Sheets

METHOD FOR TREATING BREAST CANCER BY TARGETING BREAST CANCER STEM CELL

STATEMENT REGARDING GOVERNMENT RIGHTS

This invention was made with government support of the Republic of Korea under Contract No. 1711000792 awarded by Korean Ministry of Science, ICT and Future Planning. The government has certain rights in the invention.

CROSS-REFERENCE TO RELATED APPLICATION

This application claims priority to and the benefit of Korean Patent Application No. 2014-0113554, filed on Aug. 28, 2014, the disclosure of which is incorporated herein by reference in its entirety.

BACKGROUND

1. Field of the Invention

The present invention relates to a composition for inhibiting growth of cancer stem cells, which includes an EXT1 (exostosin 1), LDHB(lactate dehydrogenase B), CD109 (Cluster of Differentiation 109), EFEMP2 (EGF-containing fibulin-like extracellular matrix protein 2), RASIP1 (Ras interacting protein 1), or SERPINE1 (serpin peptidase inhibitor, clade E (nexin, plasminogen activator inhibitor type 1), member 1) gene expression inhibitor as an active ingredient, and a method for treating cancer using the same.

2. Discussion of Related Art

Breast cancer is the most common malignant tumor, killing approximately 40,000 females every year, and thus is very important to diagnose at an early stage. However, viability in patients is still not improved when cancer is severely advanced or metastasized, even when the cancer is treated using various anti-cancer agents already known in the related art.

That is, the cause of death is not due to incipient cancer, but mainly due to recurrence or metastasis of cancer. Generally, drug resistance and cancer stem cells cause such recurrence and metastasis. Doxorubicin is a representative chemical used to treat breast cancer, and serves to remove actively dividing and proliferating breast cancer cells. The chemical has several side effects. One of the side effects is that cells having resistance to the chemical appear. According to recent reports, it is known that cancer stem cells play an important role in building resistance to the chemical.

As a representative anti-cancer therapy, chemotherapy alone or in combination with other therapeutic methods such as radiotherapy has been used as the most efficient therapeutic method to treat cancer. However, although the medicinal effect of anti-cancer drugs in chemotherapy varies according to the ability of the drugs to kill cancer cells, there is a problem in that the drugs may kill normal cells as well as the cancer cells when the drugs are used.

A hypothesis that cancer stem cells (CSCs) are cancer cells having unlimited regenerative abilities and tumors originate from stem cells was confirmed with publication of an article showing that a group of cells having a probability of converting into cancer stem cells in acute myelogenous leukemia were implanted into immunosuppressed rats and human leukemia was reproduced in the rats in the late 90s. Since then, cancer stem cells have been proven to exist in breast cancer, and stem cells in solid carcinomas have been confirmed.

Various heterogeneities of malignant tumors are coincident with various differentiative characteristics of stem cells, and the drug resistance of cancer cells that is endlessly expressed regardless of a number of target treatments is coincident with basic characteristics of the stem cells. As a result, formation of tumors may be considered to be associated with the stem cells, and cancer stem cells may become a new field of targeted therapy.

A variety of therapeutic methods have been designed based on the cancer stem cell hypothesis. Among these, a widely known method is a method in which a self-renewal pathway of the cancer stem cells is used. In this therapy, it is important to target the self-renewal of cancer stem cells while maintaining the self-renewal of normal stem cells. For example, a notch signal travels by means of an enzyme referred to as gamma secretase. In this case, when an inhibitor against gamma secretase (i.e., a gamma secretase inhibitor) is used to treat breast cancer in which Notch1 is overexpressed, it is possible to achieve an anti-tumor effect. When a hedgehog signal system is targeted, the therapeutic method is reported to have an anti-cancer effect. When a hedgehog inhibitor, cyclopamine, is administered to an animal into which tumor has been xenografted, the tumor is dramatically contracted. In addition, the hedgehog inhibitor is reported to be associated with MAPK and JAK2/STAT3 signaling pathways.

However, there are many limitations on research on cancer stem cells so far, and the roles of cancer stem cells in formation and maintenance of tumor has yet to be clearly identified. To efficiently perform treatment that targets only cancer stem cells without causing damage to normal stem cells, knowledge and understanding of molecular biological characteristics important for maintenance and regulation of cancer stem cells or regulatory pathways are required.

Also, not much research on anti-cancer agents directly targeting cancer stem cells has been conducted so far. In the prior art, various types of research on inhibiting cancer stem cells or suppressing upstream signaling proteins in the cancer stem cells to inhibit cancer stem cells were conducted as experiments for directly inhibiting target genes in cancer stem cells. However, such targeting experiments have encountered difficulties due to mutations of tumor genes and proteins in many tumor patients.

Therefore, improving the selectivity of an anti-cancer drug to cancer stem cells is sure to enable drugs to be used in smaller quantities by enhancing the medical efficacy of drugs in chemotherapy. Accordingly, an improved approach to selective inhibition of the growth of cancer stem cells to treat and prevent cancer is required.

SUMMARY OF THE INVENTION

Therefore, the present inventors, while observing the correlation between anticancer agent-resistant breast cancer and cancer stem cells and searching for cancer stem cell marker genes for treating the anticancer agent (doxorubicin)-resistant breast cancer, found that EXT1 (exostosin 1), LDHB(lactate dehydrogenase B), CD109 (Cluster of Differentiation 109), EFEMP2 (EGF-containing fibulin-like extracellular matrix protein 2), RASIP1(Ras interacting protein 1), or SERPINE1(serpin peptidase inhibitor, clade E (nexin, plasminogen activator inhibitor type 1), member 1) gene is an important marker, and investigated a molecular mechanism associated with a Wnt/PI3K/Akt signaling system. Therefore, the present invention has been completed based on these facts.

The present invention is directed to a pharmaceutical/food composition for inhibiting growth of breast cancer stem cells, which includes an EXT1, LDHB, CD109, EFEMP2, RASIP1, or SERPINE1 gene expression inhibitor (siRNA) as an active ingredient. That is, the present invention is directed to a method for targeted treatment of breast cancer stem cells using siRNA against the genes as a Wnt/PI3K/Akt signaling activity inhibitor.

To address the issues described above, in an aspect, the present invention provides a pharmaceutical composition for inhibiting growth of cancer stem cells, which includes an EXT1, LDHB, CD109, EFEMP2, RASIP1, or SERPINE1 gene expression inhibitor as an active ingredient.

In another aspect, the present invention provides a method of inhibiting growth of cancer stem cells, which includes administering the EXT1, LDHB, CD109, EFEMP2, RASIP1, or SERPINE1 gene expression inhibitor to a subject.

In still another aspect, the present invention provides a cancer stem cell growth inhibitory use of the EXT1, LDHB, CD109, EFEMP2, RASIP1, or SERPINE1 gene expression inhibitor.

In one exemplary embodiment of the present invention, the expression inhibitor may be small interfering RNA (siRNA) complementarily binding to the EXT1, LDHB, CD109, EFEMP2, RASIP1, or SERPINE1 gene.

In another exemplary embodiment of the present invention, the siRNA complementarily binding to the EXT1 gene may have a sense sequence set forth in SEQ ID NO: 1 and an anti-sense sequence set forth in SEQ ID NO: 2.

In still another exemplary embodiment of the present invention, the siRNA complementarily binding to the LDHB gene may have a sense sequence set forth in SEQ ID NO: 3 and an anti-sense sequence set forth in SEQ ID NO: 4.

In still another exemplary embodiment of the present invention, the siRNA complementarily binding to the CD109 gene may have a sense sequence set forth in SEQ ID NO: 5 and an anti-sense sequence set forth in SEQ ID NO: 6.

In still another exemplary embodiment of the present invention, the siRNA complementarily binding to the EFEMP2 gene may have a sense sequence set forth in SEQ ID NO: 7 and an anti-sense sequence set forth in SEQ ID NO: 8.

In still another exemplary embodiment of the present invention, the siRNA complementarily binding to the RASIP1 gene may have a sense sequence set forth in SEQ ID NO: 9 and an anti-sense sequence set forth in SEQ ID NO: 10.

In still another exemplary embodiment of the present invention, the siRNA complementarily binding to the SERPINE1 gene may have a sense sequence set forth in SEQ ID NO: 11 and an anti-sense sequence set forth in SEQ ID NO: 12.

In yet another exemplary embodiment of the present invention, the EXT1, LDHB, CD109, EFEMP2, RASIP1, or SERPINE may activate the cancer stem cells by means of a PI3K-β-catenin signaling pathway.

In yet another exemplary embodiment of the present invention, the cancer may be breast cancer.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 2A is a diagram showing the results obtained by comparing the viabilities of MCF7 and drug-resistant MCF7/ADR cells against an anti-cancer agent (doxorubicin) using an MTT assay, and FIG. 2B is a diagram showing the results obtained by comparing expression levels of P-glycoprotein (P-gp) in these cells using qRT-PCR and western blotting;

DETAILED DESCRIPTION OF EXEMPLARY EMBODIMENTS

Figure 1:
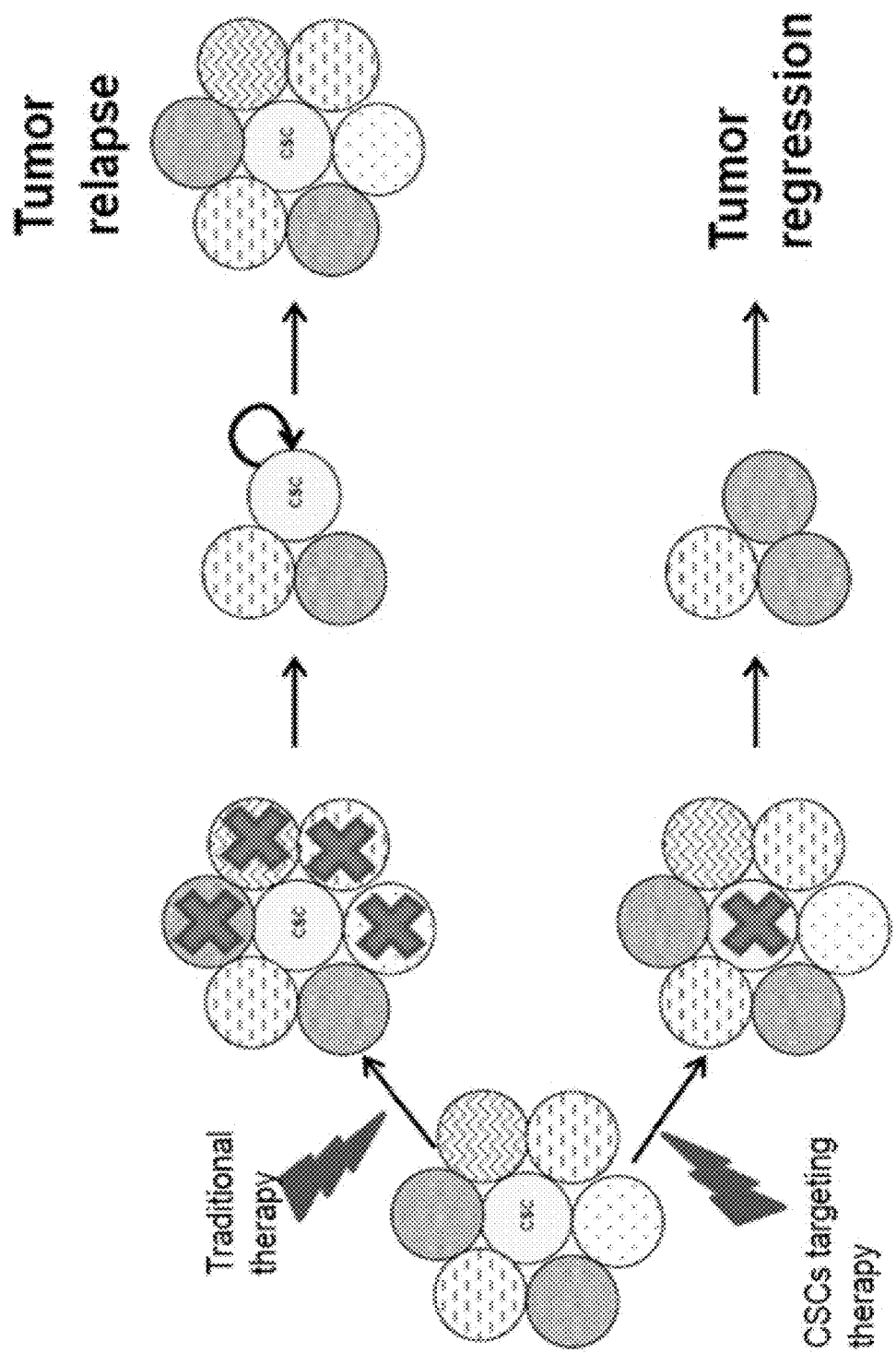
FIG. 1 is a schematic diagram showing the comparison between a conventional cancer cell-targeted therapeutic method and a cancer stem cell-targeted therapeutic method.

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclatures used in this specification and the experimental methods described below are widely known and generally used in the related art.

The present invention relates to a pharmaceutical composition for inhibiting growth of breast cancer stem cells, which includes an EXT1, LDHB, CD109, EFEMP2, RASIP1 or SERPINE1 gene expression inhibitor as an active ingredient.

The cancer stem cells are a small number of cells important for the growth and metastasis of a tumor, and form colonies through self-proliferation of tumor to cause metastasis. The cancer stem cells are a group of cells in a small group of cancer tissues playing an important role in resistance, recurrence and incidence of cancer. Selective targeted treatment of the cancer stem cells may be highly helpful in overcoming resistance to cancer and treating cancer.

Therefore, the present inventors have determined anti-cancer activities specific to cancer stem cells and a mechanism for the anti-cancer activities by treating the cancer stem cells with an EXT1, LDHB, CD109, EFEMP2, RASIP1 or SERPINE1 gene expression inhibitor to treat breast cancer and the like using cancer stem cell-targeted treatment. That is, for the present invention, an effect and mechanism of the EXT1, LDHB, CD109, EFEMP2, RASIP1 or SERPINE1 gene expression inhibitor on the cancer stem cells were researched.

As a result, there was no change in cell viability of common cancer cells due to treatment of the EXT1, LDHB, CD109, EFEMP2, RASIP1 or SERPINE1 gene expression inhibitor, but the cancer stem cell-specific anti-cancer activities were confirmed due to decreases in colony size and the number of cancer stem cells. Particularly, an inhibitory effect on breast cancer stem cells was verified through a decrease in a breast-cancer-stem-cell-specific surface antigen (CD44+/24−) and a marker enzyme (aldehyde dehydrogenase (ALDH)).

Also, a change in expression of proteins associated with the cancer stem cells was observed through western blotting to determine an anti-cancer activity mechanism (i.e., a Wnt/PI3K/Akt signaling system). As a result, a signaling activity inhibitory mechanism of the proteins was confirmed.

More particularly, in the present invention, candidate genes capable of regulating the cancer stem cells in breast cancer cells having resistance to the anti-cancer agent (doxorubicin) were searched for, and the functions of the genes were studied. This was done in search of a method capable of removing the cancer stem cells to overcome drug resistance and even prevent recurrence of cancer to effectively overcome cancer.

For this purpose, it was first determined that the breast cancer cells which were continuously exposed to a low concentration of doxorubicin exhibited stronger drug resistance than maternal cells using an MTT assay and by means of expression of P-glycoprotein (P-gp) that is a resistance marker. Based on previous research reports showing that there is a correlation between resistant cells and cancer stem cells, the cancer stem cells of the resistant cells exhibiting resistance to doxorubicin were compared to those of the maternal cells by means of a CD44+/CD24− assay and an ALDEFLOUR assay. As a result, it could be seen that the resistant cells included a larger number of the cancer stem cells than the maternal cells. Likewise, the self-proliferation ability that is one of the characteristics of the cancer stem cells was also determined. As a result, it was revealed that the resistant cells had a higher self-proliferation ability than the maternal cells.

Also, in the genes having a correlation with the stem cells selected among the genes whose expression increased 6-fold or more in the resistant cells compared to the maternal cells, the EXT1, LDHB, CD109, EFEMP2, RASIP1 and SERPINE1 genes in which P-gp was expressed at a decreased level were selected through a DNA microarray to determine which role the EXT1, LDHB, CD109, EFEMP2, RASIP1 and SERPINE1 genes play in the cancer stem cells.

To examine whether EXT1, LDHB, CD109, EFEMP2, RASIP1 and SERPINE1 are associated with an aggressive malignant tumor, mRNA expressions of stem cell markers (CD44, integrin-α6), a resistance marker(P-gp), and epithelial mesenchymal transition markers (Vimentin, N-cadherin, E-cadherin) was determined. As a result, it was revealed that the resistant cells are present in the form of aggressive malignant tumor. In this case, it was confirmed that, when EXT1 and LDHB were knocked down (silenced) with siRNA, the form of aggressive malignant tumor was reduced.

To determine how EXT1, LDHB, CD109, EFEMP2, RASIP1 and SERPINE1 are associated with the cancer stem cells, the genes were silenced in the resistant cells, and the cancer stem cells were counted. As a result, it could be seen that the number of the cancer stem cells decreased, and the self-proliferation ability was also lowered.

Further, to determine through which pathway such functions are achieved, a Wnt signaling pathway and a PI3K/Akt signaling pathway, both of which have a high correlation with the stem cells, were examined. As a result, it was revealed that β-catenin was expressed at an increased level, and the activities of PI3K and Akt inhibiting expression of β-catenin were lowered in the resistant cells including the cancer stem cells. On the other hand, it could be seen that the silencing of EXT1, LDHB, CD109, EFEMP2, RASIP1 or SERPINE1 caused an increase in the activities of PI3K and Akt, thereby decreasing expression of β-catenin as well. That is, the in vitro correlation of EXT1, LDHB, CD109, EFEMP2, RASIP1 or SERPINE1 whose expression is increased in the resistant cells with the form of aggressive malignant tumor, particularly the cancer stem cells, was examined. As a result, it was revealed that the six genes regulated the cancer stem cells through the Wnt/PI3K/Akt signaling pathway. Based on the fact that the silencing of each of the 6 genes causes a decrease in the number of the cancer stem cells and also a reduction in the self-proliferation ability, it was confirmed that the six genes are able to be new therapeutic targets for removing the cancer stem cells.

Therefore, according to one exemplary embodiment of the present invention, when the EXT1, LDHB, CD109, EFEMP2, RASIP1 or SERPINE1 gene expression inhibitor is used as the anti-cancer agent, the above-described method will be a useful anti-cancer therapeutic method capable of preventing metastasis of cancer while reducing side effects by an alteration of a pathway having an influence on the cancer stem cells at a concentration which is not toxic to the cancer cells.

In this specification, the term 'treating or preventing breast cancer' encompasses a meaning that it includes relieving and alleviating breast cancer and improving symptoms of breast cancer, and also includes lowering a probability of developing breast cancer.

According to one exemplary embodiment of the present invention, the composition for treating or preventing breast cancer may be formulated into a pharmaceutical composition. For use in treating and prevention of breast cancer, the active ingredient according to one exemplary embodiment of the present invention may be administered by itself, or the component may be included as the active ingredient according to one exemplary embodiment of the present invention.

The pharmaceutical composition includes the EXT1, LDHB, CD109, EFEMP2, RASIP1 or SERPINE1 gene expression inhibitor as the active ingredient, and may further include a pharmaceutically available carrier. The pharmaceutically available carrier is widely used to form a preparation. In this case, the pharmaceutical composition includes a saline solution, sterile water, a Ringer's solution, a buffered saline solution, cyclodextrin, a dextrose solution, a maltodextrin solution, glycerol, ethanol, a liposome, and the like, but the present invention is not limited thereto. As necessary, the pharmaceutical composition may further include other typical additives such as an antioxidant, a buffer, and the like. Also, a diluent, a dispersant, a surfactant, a binder, a lubricant, and the like may be further added into the composition, which may be formulated into injectable formulations such as an aqueous solution, a suspension, an emulsion, etc., pills, capsules, granules, or tablets. For the proper pharmaceutically available carrier and the formulation, the composition may preferably be formulated according to the respective components using a method such as one disclosed in Remington's Pharmaceutical Science (Mack Publishing Company, Easton Pa.). The pharmaceutical composition according to one exemplary embodiment of the present invention may be formulated into injections, inhalations, or external preparations for skin, but the present invention is not limited thereto.

A method of administering the pharmaceutical composition according to the present invention is not particularly limited. However, the pharmaceutical composition may be administered orally or parenterally, for example, intravenously, subcutaneously, or intraperitoneally, or by inhalation, skin or local application, according to a desired method.

The dose of the composition may vary according to the body weight, age, sex, health condition, diet, administration time, administration method, excretion rate, and severity of a disease of a patient. The daily dose refers to an amount of a therapeutic material according to the present invention sufficient for treatment that relieves symptoms when administered to a subject in need of treatment. Also, the effective dose of the therapeutic material may vary according to certain compounds, conditions, and severity of the conditions, and may be generally determined by those skilled in the related art. As a non-limiting example, the dose of the composition according to the present invention to be administered into the human may vary according to the age, body weight, sex, form of administration, health condition, and severity of a disease of a patient. When the composition is administered to an adult patient weighing 70 kg, the composition may be generally administered daily at a dose of 0.01 to 1000 mg/day, preferably a dose of 1 to 500 mg/day. In this case, the composition may be administered at intervals of once a day, or administered in divided doses.

Hereinafter, preferred embodiments are provided to aid in understanding the present invention. However, it should be understood that detailed description provided herein is merely intended to provide a better understanding of the present invention, and is not intended to limit the scope of the present invention.

EXAMPLE 1

Experimental Method 1-1: Establishment of Drug-Resistant Breast Cancer Cell Line (MCF7/ADR)

A human breast cancer maternal cell line, MCF-7 (Korean Cell Line Bank), was continuously exposed to 1 µM of a drug, doxorubicin (Sigma). In this case, the maternal cell line was cultured in a drug-free medium for at least one week to establish a breast cancer cell MCF7/ADR having induced drug resistance. Here, the cell culture was performed at 37° C. and 5% $CO_2$ in a DMEM medium (Hyclon, Logan, Utah) supplemented with 10% FBS and 1% penicillin.

1-2: MTT Assay: Analysis of Cell Viability

To evaluate cytotoxicity of the anti-cancer agent (doxorubicin), a cell viability assay was performed using an MTT assay. First, cells were plated on a 96-well plate at a density of $5 \times 10^3$ cells/well, treated with the drug, and then cultured for 24, 48, and 72 hours. Thereafter, each well was treated with 5 mg/ml of MTT (AMRESCO), and the cells were cultured at 37° C. for 4 hours. Each well was treated with DMSO (100 ml/well) to dissolve a formazan salt, and the amount of the formazan salt was determined by measuring an OD value at 540 nm using a microplate reader (Tecan Austria GmbH, Austria).

1-3: Quantitative Real-Time PCR (qRT-PCR)

Total RNAs were extracted from the cultured cells using a TRIzoL reagent (Invitrogen), and cDNAs were synthesized using a cDNA synthetic kit (Promega) for reverse transcription-PCR.

The synthesized cDNAs were subjected to real-time PCR using certain primers as listed in the following Table 1. In this case, the real-time PCR was performed in a Bio-Rad Real-Time PCR system using a SYBR Green PCR Master mix (Applied Biosystems), and the data was obtained by calculating an average value for separate experiments performed in at least triplicate.

TABLE 1

Primer sequence for qRT-PCR

| Name | | Sequence |
|---|---|---|
| P-gp | Forward | 5'-TGGGAAGATCGCTACTGAAGC-3'; SEQ ID NO 13 |
| | Reverse | 5'-TTTCCTCAAAGAGTTTCTGTATGGTA-3'; SEQ ID NO 14 |
| CYR61 | Forward | 5'-ACTTCATGGTCCCAGTGCTC-3'; SEQ ID NO 15 |
| | Reverse | 5'-AAATCCGGGTTTCTTTCACA-3'; SEQ ID NO 16 |
| Vimentin | Forward | 5'-TGTCCAAATCGATGTGGATGTTTC-3'; SEQ ID NO 17 |
| | Reverse | 5'-TTGTACCATTCTTCTGCCTCCTG-3'; SEQ ID NO 18 |

TABLE 1-continued

Primer sequence for qRT-PCR

| Name | | Sequence |
|---|---|---|
| N-cadherin | Forward | 5'-ACAGTGGCCACCTACAAAGG-3'; SEQ ID NO 19 |
| | Reverse | 5'-CCGAGATGGGGTTGATAATG-3'; SEQ ID NO 20 |
| E-cadherin | Forward | 5'-GAGAGCGGTGGTCAAAGAGC-3'; SEQ ID NO 21 |
| | Reverse | 5'-GAGGAGTTCAGGGAGCTCAG-3'; SEQ ID NO 22 |
| GAPDH | Forward | 5'-AATCCCATCACCATCTTCCA-3'; SEQ ID NO 23 |
| | Reverse | 5'-TGGACTCCACGACGTACTCA-3'; SEQ ID NO 24 |
| CD109 | Forward | 5'-GTGCTGATGGCAACCAACTG-3'; SEQ ID NO 25 |
| | Reverse | 5'-CTCAAAAGGCGATCCCACCT-3'; SEQ ID NO 26 |
| EXT1 | Bioneer Gene ID: 2131, #P237660 | |
| LDHB | Bioneer Gene ID: 3945, #P224700 | |
| EFEMP2 | Bioneer Gene ID: 30008, #P129515 | |
| RASIP1 | Bioneer Gene ID: 54922, #P289502 | |
| SERPINE1 | Bioneer Gene ID: 5054, #P321087 | |

1-4: Western Blot Analysis

Proteins were electrophoresed on SDS-PAGE, and the separated proteins were transferred to a nitrocellulose membrane (Whatman), and then blocked at room temperature for 15 minutes in a TBS-5% non-fat milk solution supplemented with 0.1% Tween-20. The membrane was cultured overnight with a primary antibody at 4° C., cultured with a horseradish peroxidase-conjugated secondary antibody at room temperature for an hour, and developed using a West Pico chemiluminescent substrate (PIERCE).

The primary antibodies used herein were P-gp (Cell Signaling Technology, #12683, 1:1000), p-PI3K (Santa Cruz Biotechnology, sc-12929, 1:500), PI3K (Santa Cruz Biotechnology, sc-1637, 1:500), p-Akt (Cell Signaling Technology, #9271, 1:1000), Akt (Cell Signaling Technology, #9272, 1:1000), β-catenin (Cell Signaling Technology, #9562, 1:1000), and β-actin (Santa Cruz Biotechnology, sc-47778, 1:500).

1-5: CD44+/CD24− Assay (Flow Cytometric Assay)

To detect cancer stem cells (CSCs) in the MCF7 and MCF7/ADR cells, a breast cancer stem cell surface antigen, CD44+/CD24−, was assayed.

Specifically, the $1 \times 10^6$ cells were labeled with anti-human CD44-APC and CD24-PE (BD biosciences). In this case, the antibody was diluted with a 5% BSA solution. The cells were cultured at room temperature for 25 minutes, washed, re-suspended in 500 ml of 5% BSA, and then detected using BD FACS Aria III.

1-6: ALDEFLUOR Assay

To prove a cancer stem cell-specific growth inhibitory effect, it was determined whether a breast cancer stem cell marker enzyme ALDH+ population was reduced using an ALDEFLOUR assay kit (Stem Cell technologies).

Specifically, the cells were stained with 1.5 mM bodipyaminoacetaldehyde (BAAA), and then cultured at 37° C. for 45 minutes. An ALDH1 inhibitor, diethylaminobenzaldehyde (DEAB), was used as the negative control.

The $1 \times 10^6$ stained cells were assayed using BD FACS Aria III. In this case, the positive fluorescent ALDH1-expressed cells (ALDH+) were detected in a green fluorescent channel (520 to 540 nm).

1-7: Mammosphere Formation Assay

Since the breast cancer stem cells formed a mass of colonies in the form of floating spheres without attaching to a surface of a plate, the size and number of the masses were observed by a mammosphere formation assay to determine a cancer-stem-cell-specific effect.

Specifically, a single-cell suspension was cultured at a density of 1,000 to 15,000 cells/well (on an ultralow attachment culture plate (Corning CoStar)) using a MammoCult™ Human Medium kit (Stem Cell Technologies), and the spherical cells were counted and observed under a microscope.

1-8: mRNA Knockdown by siRNA

EXT1, LDHB, CD109, EFEMP2, RASIP1, and SERPINE1 gene knockdown experiments were performed using siRNA (Bioneer Corp.): siEXT1 (Gene ID 2131, siRNA No. 1049149, 20 nM), siLDHB (Gene ID 3945, siRNA No. 1083399, 20 nM), siCD109 (Gene ID 135228, siRNA No. 1027641, 20 nM), siEFEMP2 (Gene ID 30008, siRNA No. 1045872, 20 nM), siRASIP1 (Gene ID 54922, siRNA No. 1126933, 20 nM), siSERPINE1 (Gene ID 5054, siRNA No. 1135690, 20 nM), and the negative control (#SN-1001, 20 nM).

siRNA transfection was performed using a Neon® Transfection system (Life technologies). After 48 hours, the expression of each gene was analyzed using qRT-PCR.

1-9: DNA Microarray

Total RNAs were prepared from the MCF7 and MCF7/ADR cells using a Trizol reagent (Invitrigen), and DNA expression levels of the MCF7 and MCF7/ADR cells were compared using an Affymatrix Human ST2.0 DNA microarray. Also, PCR was performed in an Applied Biosystems 7300 Real-Time PCR system using a SYBR Green PCR Master mix (Applied Biosystems). Each experiment was performed in triplicate, and an average value of the data was calculated.

EXAMPLE 2

Determination of Drug Resistance Characteristics of MCF7/ADR Breast Cancer Cells To determine whether the MCF7/ADR cells had drug resistance against the doxorubicin anti-cancer agent, a time-dependent, dose-dependent MTT assay was performed on human luminal breast cancer cells MCF7, and MCF7/ADR cells having resistance to doxorubicin.

After 24, 48, and 72 hours when the MCF7 and MCF7/ADR cells were treated with doxorubicin (0, 1, 2, 10, and 25 μM), the cell viabilities were determined. As a result, it was revealed that the MCF7/ADR cells had higher cell viability against doxorubicin than the MCF7 cells, as shown in FIG. 2A.

Since P-glycoprotein (P-gp) is known to be a marker for breast cancer having resistance to doxorubicin, expression levels of mRNAs and proteins were determined using qRT-PCR and a western blot assay so as to examine whether P-gp was overexpressed in the MCF7/ADR cells.

Figure 2:
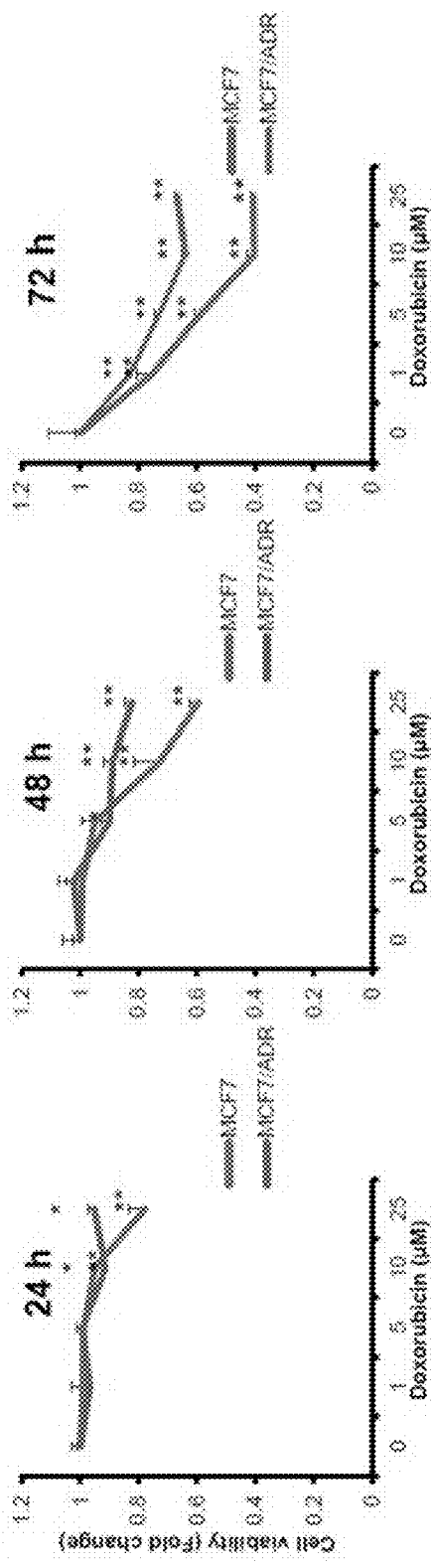
FIG. 2 comprises FIG. 2A and FIG. 2B.
Figure 2:
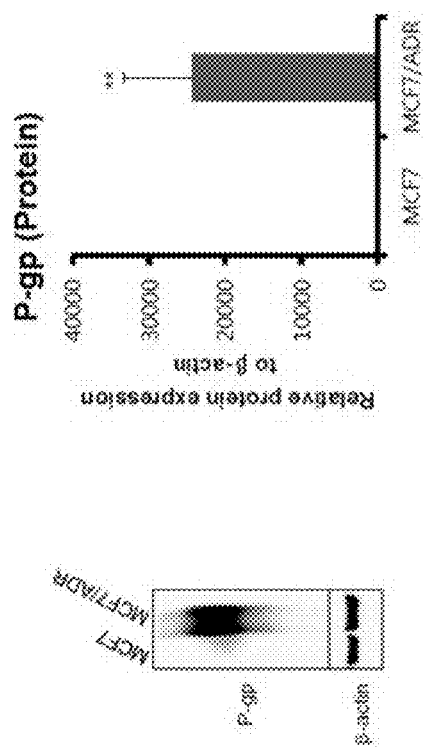
Figure 2:
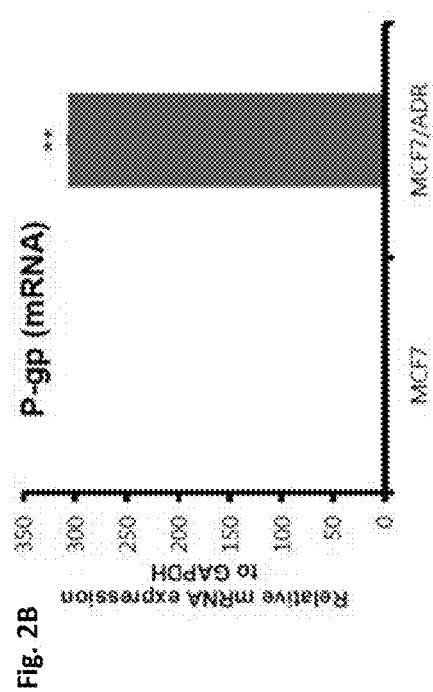

As a result, it was revealed that the MCF7/ADR cells had higher P-gp mRNA and protein expression levels than the MCF7 cells, as shown in FIG. 2B, indicating clearly that the MCF7/ADR cells had chemical resistance to doxorubicin.

EXAMPLE 3

Determination of Presence of Cancer Stem Cells in Drug-Resistant MCF7/ADR Breast Cancer Cells 3-1. Marker (CD44+/CD24− or ALDH+) of Breast Cancer Stem Cells Since a breast cancer stem cell-specific surface antigen, CD44+/CD24−, and a marker enzyme, aldehyde dehydrogenase (ALDH+), were known to be markers of the breast cancer stem cells, a CD44/CD24 assay and an ALDE-FLOUR assay were performed to determine whether the MCF7/ADR cells having the drug resistance had a population of cancer stem cells.

Figure 3A:
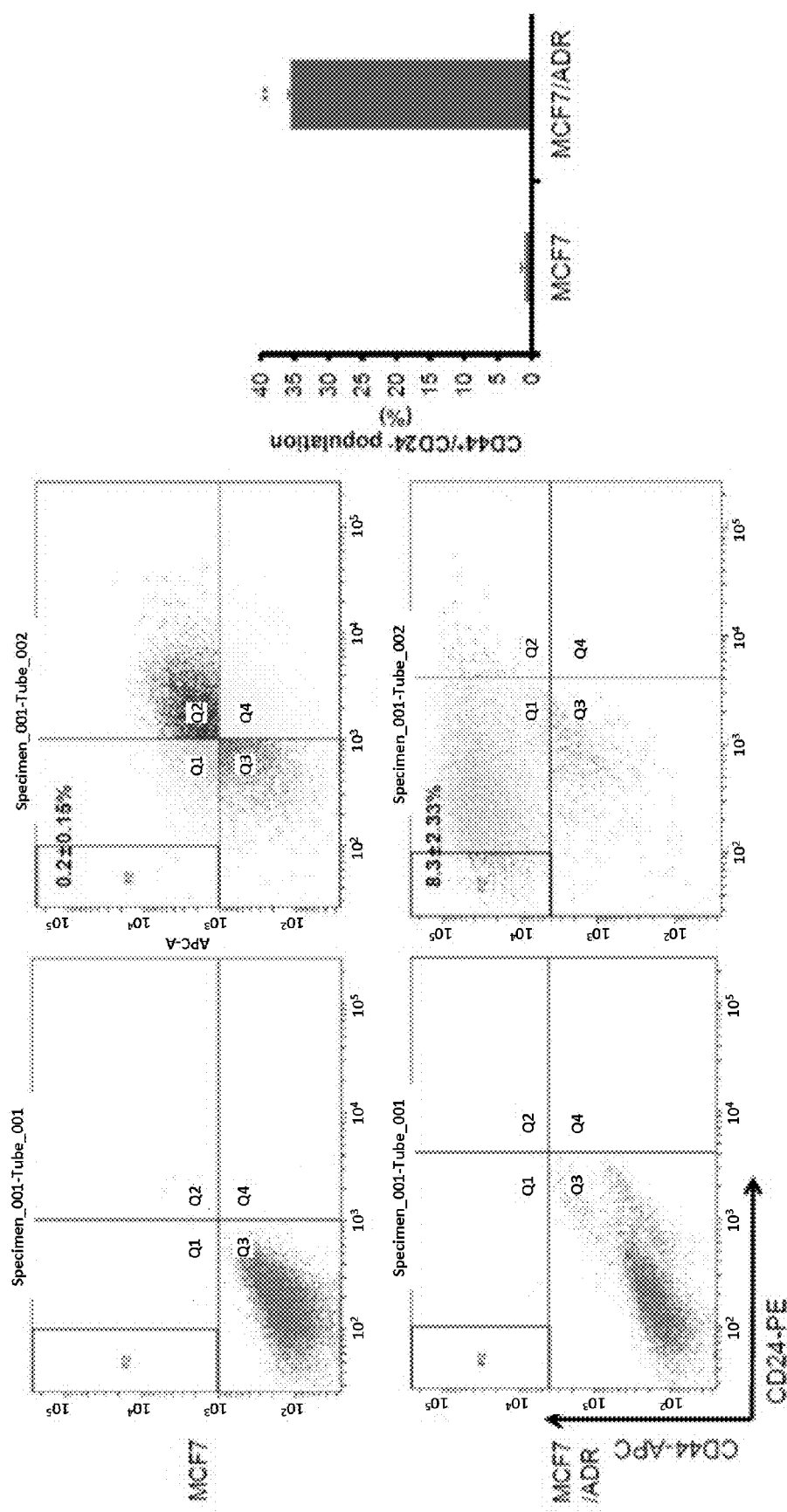
FIG. 3A is a diagram showing the results obtained by comparing the CD44+/CD24− populations in the MCF7 and drug-resistant MCF7/ADR cells.
Figure 3B:
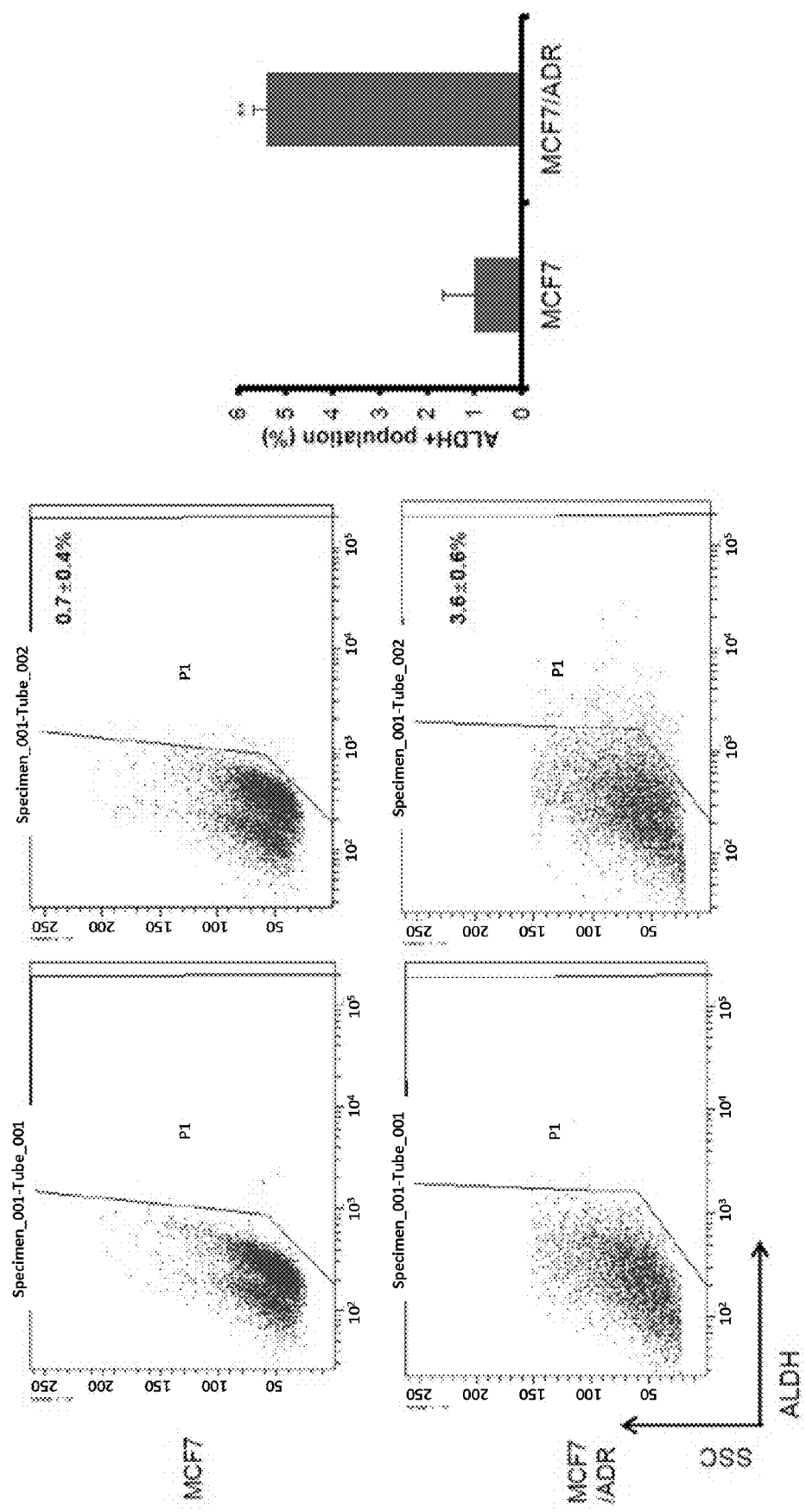
FIG. 3B is a diagram showing the results obtained by comparing the ALDH+ populations in these cells.

As a result, it was revealed that the CD44+/CD24− population of the MCF7 cells amounted to approximately 0.2%, but the CD44+/CD24− population of the MCF7/ADR cells increased to approximately 8.3%, as shown in FIG. 3A. Also, it was revealed that the ALDH+ population of the MCF7 cells amounted to approximately 0.7%, but the ALDH+ population of the MCF7/ADR cells increased to approximately 3.6%, as shown in FIG. 3B.

Therefore, it could be seen that the maternal MCF7 cells hardly had cancer stem cells, but the MCF7/ADR cells having the drug resistance had a significantly increased cancer stem cell population.

3-2. Self-Renewal Capacity (Mammosphere Formation Assay)

Since the self-renewal capacity was one of the characteristics of the cancer stem cells (CSCs), a mammosphere formation assay was performed to determine whether the drug-resistant MCF7/ADR cells had a self-renewal capacity. Since the breast cancer stem cells formed a mass of colonies in the form of floating spheres without attaching to a surface of a plate, the size and number of the masses were able to be observed to determine the presence of the cancer stem cells.

Figure 4:
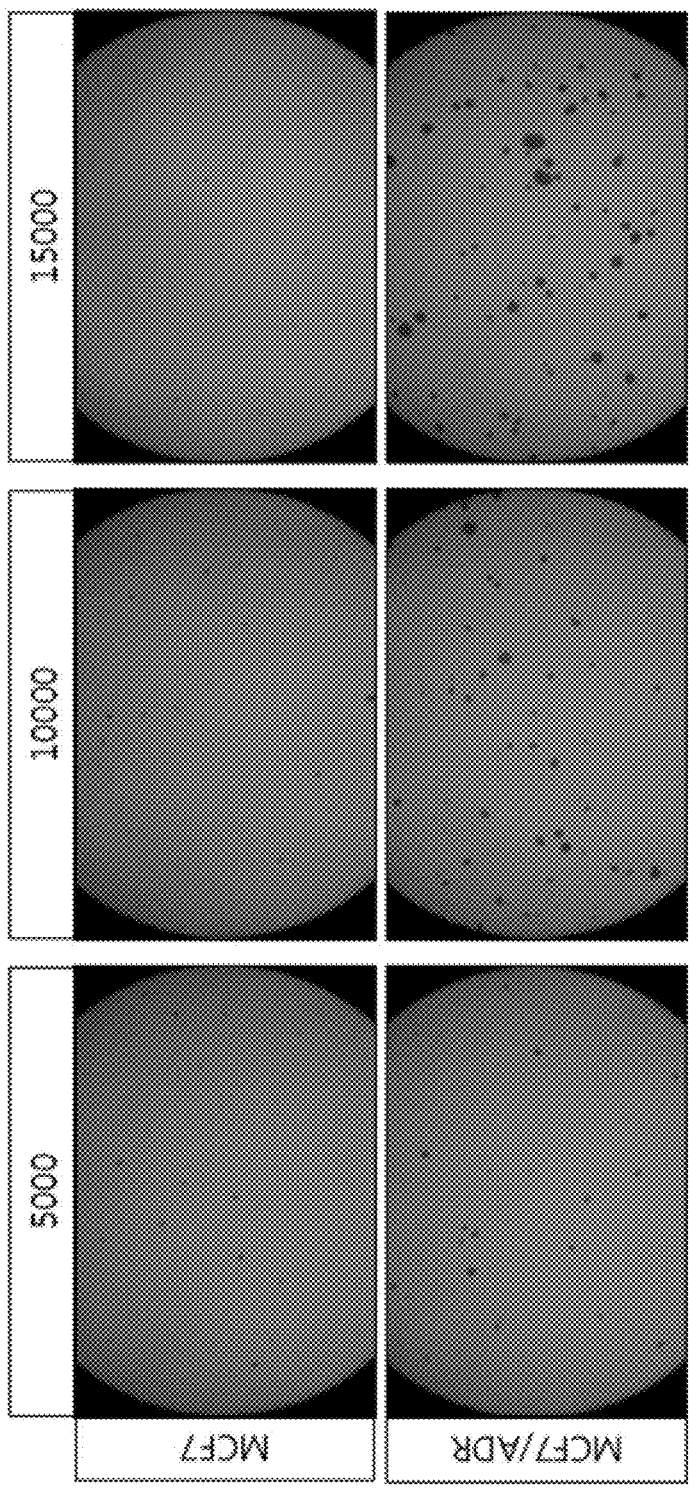
FIG. 4 is an image showing the results obtained by comparing the abilities of the MCF7 and drug-resistant MCF7/ADR cells to form mammospheres.

As a result, it was revealed that the MCF7/ADR cells had a higher mammosphere formation capacity than the MCF7 cells, as shown in FIG. 4. Therefore, it could be seen that the drug-resistant MCF7/ADR cells included the cancer stem cell population having excellent self-renewal capacity compared to the MCF7 cells.

EXAMPLE 4

Determination of Presence of Stemness-Related Genes in Drug-Resistant MCF7/ADR Breast Cancer Cells To examine DNA expression profiles in the MCF7 and MCF7/ADR cells, the DNA expression levels of genes were compared, and measured using an Affimatrix DNA microarray.

Figure 5:
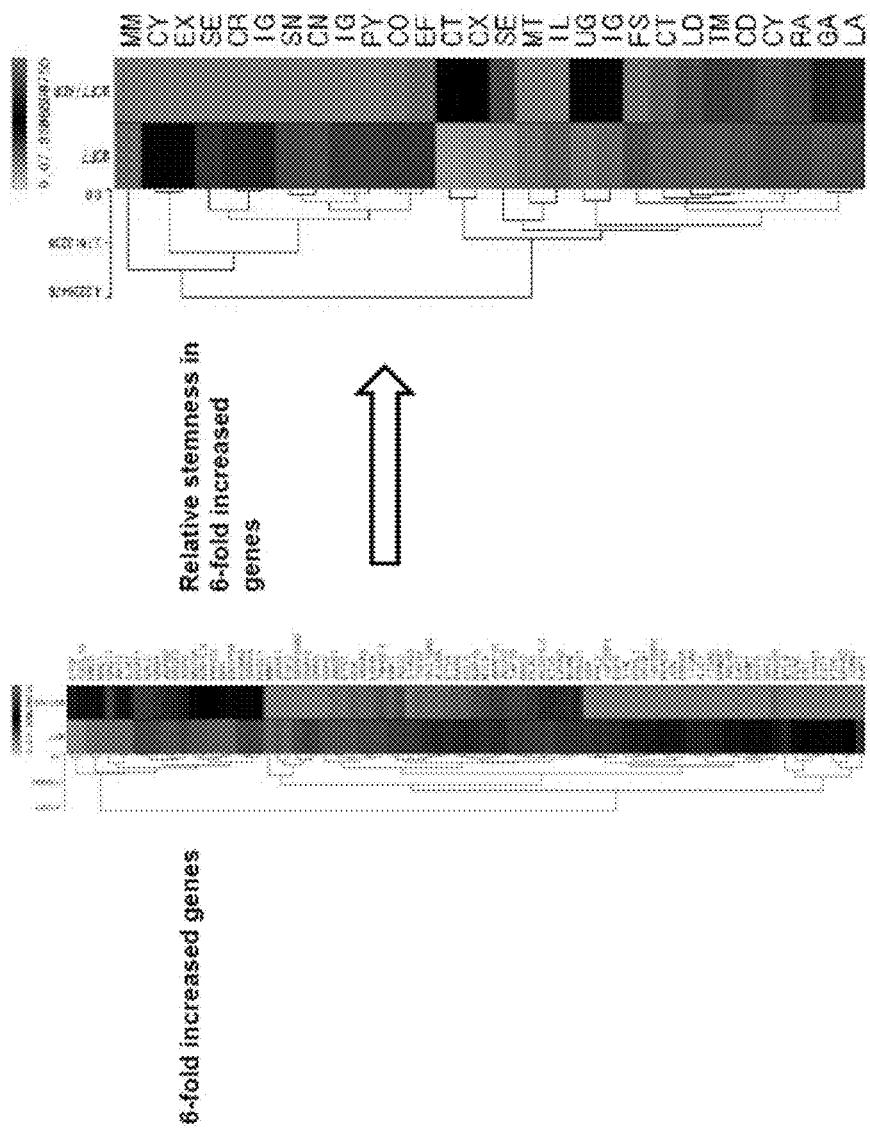
FIG. 5 is a diagram showing a profile of genes whose expression increased 6-fold or more in the drug-resistant MCF7/ADR cell.

As a result, it was determined that there were 436 genes whose expression increased approximately 6-fold or more in the MCF7/ADR cells, compared to the MCF7 cells. Among these, genes associated with stemness were further screened with the focus on the innate resistance of the cancer stem cells (see FIG. 5 and Table 2).

TABLE 2

| Gene symbol | Fold change | Gene Description |
| --- | --- | --- |
| MMP1 | 360.798 | matrix metallopeptidase 1 (interstitial collagenase) |
| MT1L | 83.348 | metallothionein 1 L (gene/pseudogene) |
| CTGF | 54.265 | connective tissue growth factor |
| IL18 | 49.968 | interleukin 18 (interferon-gamma-inducing factor) |
| SERPINE1 | 46.462 | serpin peptidase inhibitor, clade E (nexin, plasminogen activator inhibitor type 1), member 1 |
| SNAI2 | 41.077 | snail homolog 2 (*Drosophila*) |
| CNN3 | 39.941 | calponin 3, acidic |
| PYGL | 26.162 | phosphorylase, glycogen, liver |
| FSTL1 | 25.827 | follistatin-like 1 |
| EXT1 | 24.085 | exostosin 1 |
| LDHB | 21.307 | lactate dehydrogenase B |
| TM4SF1 | 17.948 | transmembrane 4 L six family member 1 |
| CYBRD1 | 15.069 | cytochrome b reductase 1 |
| RASIP1 | 14.535 | Ras interacting protein 1 |
| EFEMP2 | 14.051 | EGF containing fibulin-like extracellular matrix protein 2 |
| LAMB3 | 12.540 | laminin, beta 3 |
| CD109 | 16.609 | Cluster of Differentiation 109 |

Figure 6:
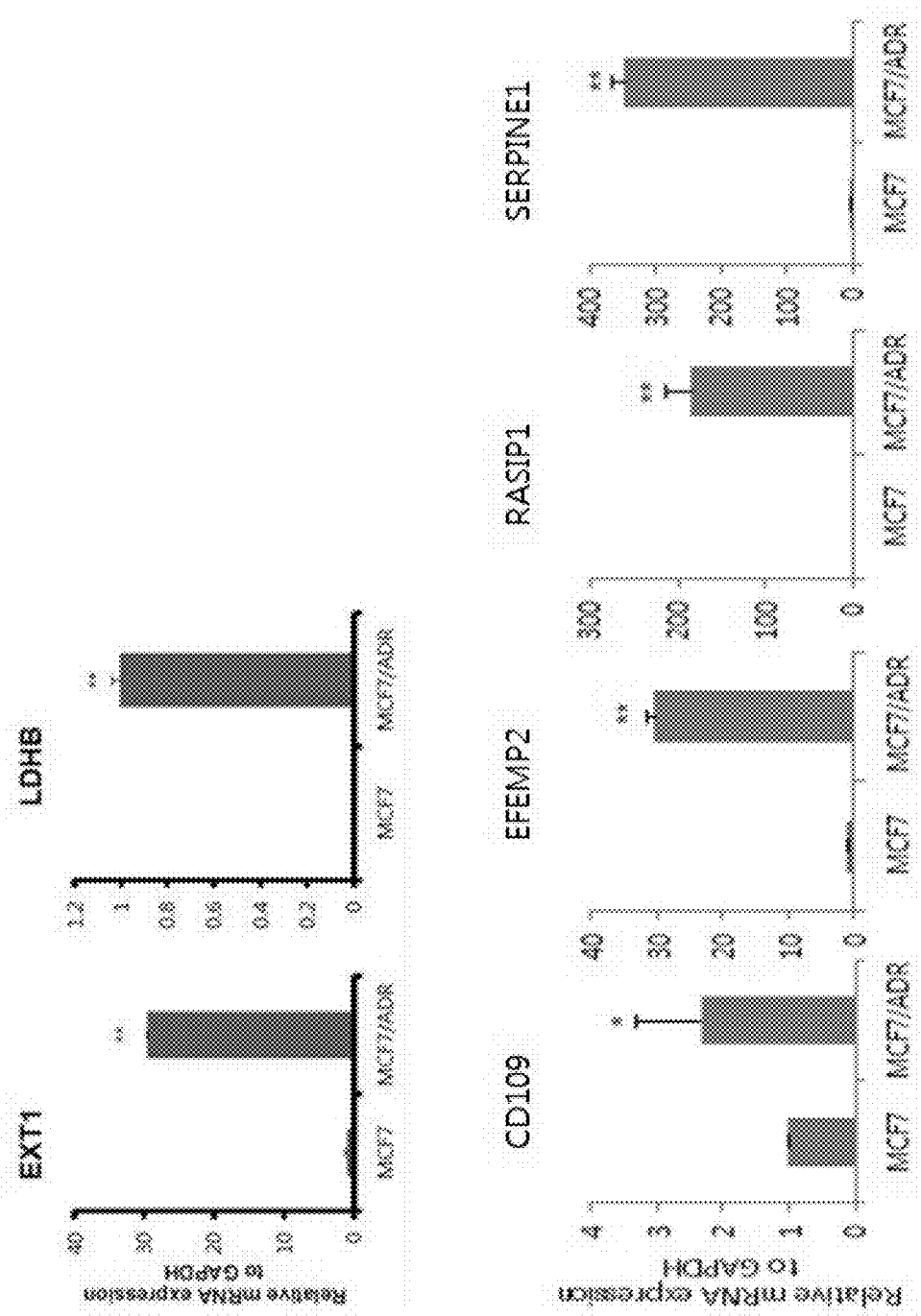
FIG. 6 is a graph illustrating the results obtained by quantifying the qRT-PCR results of the genes (EXT1, LDHB, CD109, EFEMP2, RASIP1, SERPINE1) whose expression increased 6-fold or more in the drug-resistant MCF7/ADR cell.

Also, the six genes EXT1, LDHB, CD109, EFEMP2, RASIP1, and SERPINE1 were further selected, and subjected to qRT-PCR. As a result, it was confirmed that all six of the genes were expressed at an increased level in the MCF7/ADR cells (see FIG. 6).

EXAMPLE 5

Determination of Silencing Effect of the Six Genes 5-1. Measurement of Expression Level of P-Glycoprotein (P-gp)

Since P-glycoprotein (P-gp) is known to be a marker for breast cancer having resistance to doxorubicin, P-gp was used to detect the cancer stem cells (CSCs). That is, when the presence of the cancer stem cells was determined using a Hoechst 33342 stain, P-gp served as an efflux pump for the Hoechst 33342 stain. In this case, the cancer stem cells were detected based on a characteristic in which the cancer stem cells were not stained.

To further evaluate whether the six genes finally screened in Example 4 regulated the drug resistance and the size and number of CSC populations, the genes were knocked down with siRNA, and an expression level of P-gp was determined using western blotting. That is, the MCF7/ADR cells were transfected with siRNA of each gene, and an expression level of P-gp was measured.

Figure 7:
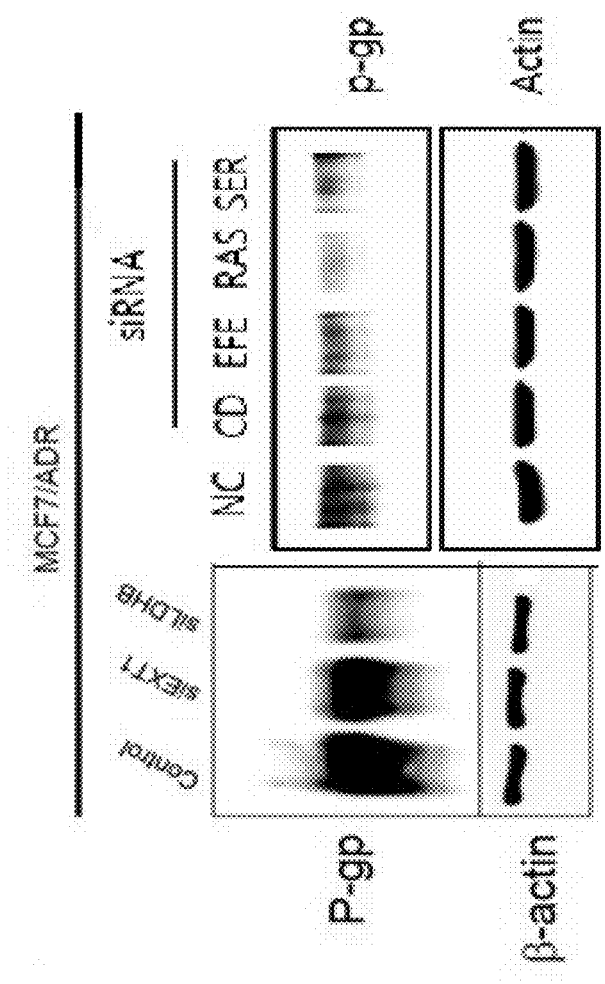
FIG. 7 is a diagram showing changes in expression of P-glycoprotein (P-gp) after the respective genes (EXT1, LDHB, CD109, EFEMP2, RASIP1, SERPINE1) whose expression increased 6-fold or more in the drug-resistant MCF7/ADR cell are treated with siRNA.

As a result, it was revealed that the expression of P-glycoprotein was down-regulated in the MCF7/ADR cells when each of the EXT1, LDHB, CD109(CD), EFEMP2 (EFE), RASIP1(RAS) and SERPINE1 (SER) genes was silenced (knocked down) with siRNA, as shown in FIG. 7. In this case, the base sequences of the siRNAs are shown in the following Table 3.

TABLE 3

| SEQ ID NO. | Sequence | siRNA |
|---|---|---|
| 1 | 5'-CACUUCUGGAUAACUCUA-3' | Sense sequence of siEXT1 |
| 2 | 5'-UAGAGUUAUCCCAGAAGUG-3' | Anti-sense sequence of siEXT1 |
| 3 | 5'-GAUUCAUCCCGUGUCAACA-3' | Sense sequence of siLDHB |
| 4 | 5'-UGUUGACACGGGAUGAAUC-3' | Anti-sense sequence of siLDHB |
| 5 | 5'-GAGUACUGGAGCGGAUCUA-3' | Sense sequence of siCD109 |
| 6 | 5'-UAGAUCCGUCCAGUACUC-3' | Anti-sense sequence of siCD109 |
| 7 | 5'-CCCAAACCUGUGUCAACUU-3' | Sense sequence of siEFEMP2 |
| 8 | 5'-AAGUUGACACAGGUUUGGG-3' | Anti-sense sequence of siEFEMP2 |
| 9 | 5'-CUGGAUAGUAACCCUUUCA-3' | Sense sequence of siRASIP1 |
| 10 | 5'-UGAAAGGGUUACUAUCCAG-3' | Anti-sense sequence of siRASIP1 |
| 11 | 5'-CACACAAAAGGUAUGAUCA-3' | Sense sequence of siSERPINE1 |
| 12 | 5'-UGAUCAUACCUUUUGUGUG-3' | Anti-sense sequence of siSERPINE1 |

These results suggested that the six genes selected finally in Example 4 had an influence on the drug resistance and CSC population in breast cancer.

5-2. Measurement of Expression Levels of CSC-, Resistance- and EMT-Related Markers Epithelial-mesenchymal transition (EMT) is an indicator of aggressive malignant tumors, and known to play an important role in embryogeny, cancer metastasis, radiation resistance, chemical resistance, etc. An EMT procedure accompanies the loss of an epithelial marker (E-cadherin), acquisition of mesenchymal markers (N-cadherin, Snail, and slug), and a dramatic change in phenotypes including modification of cell shapes. Particularly, EMT induction in the tumor cells results in radiation/chemical resistance, as well as active infiltration and metastasis.

Therefore, to determine whether EXT1, LDHB, CD109, EFEMP2, RASIP1, and SERPINE1 were associated with the aggressive phenotype of cancer, the mRNA expression levels of cancer stem cell markers (CD44, and Integrin-α6 (ITGA6)), a resistance marker (P-gp), and EMT markers (Vimentin, N-cadherin, and E-cadherin) were determined using qRT-PCR.

Figure 8A:
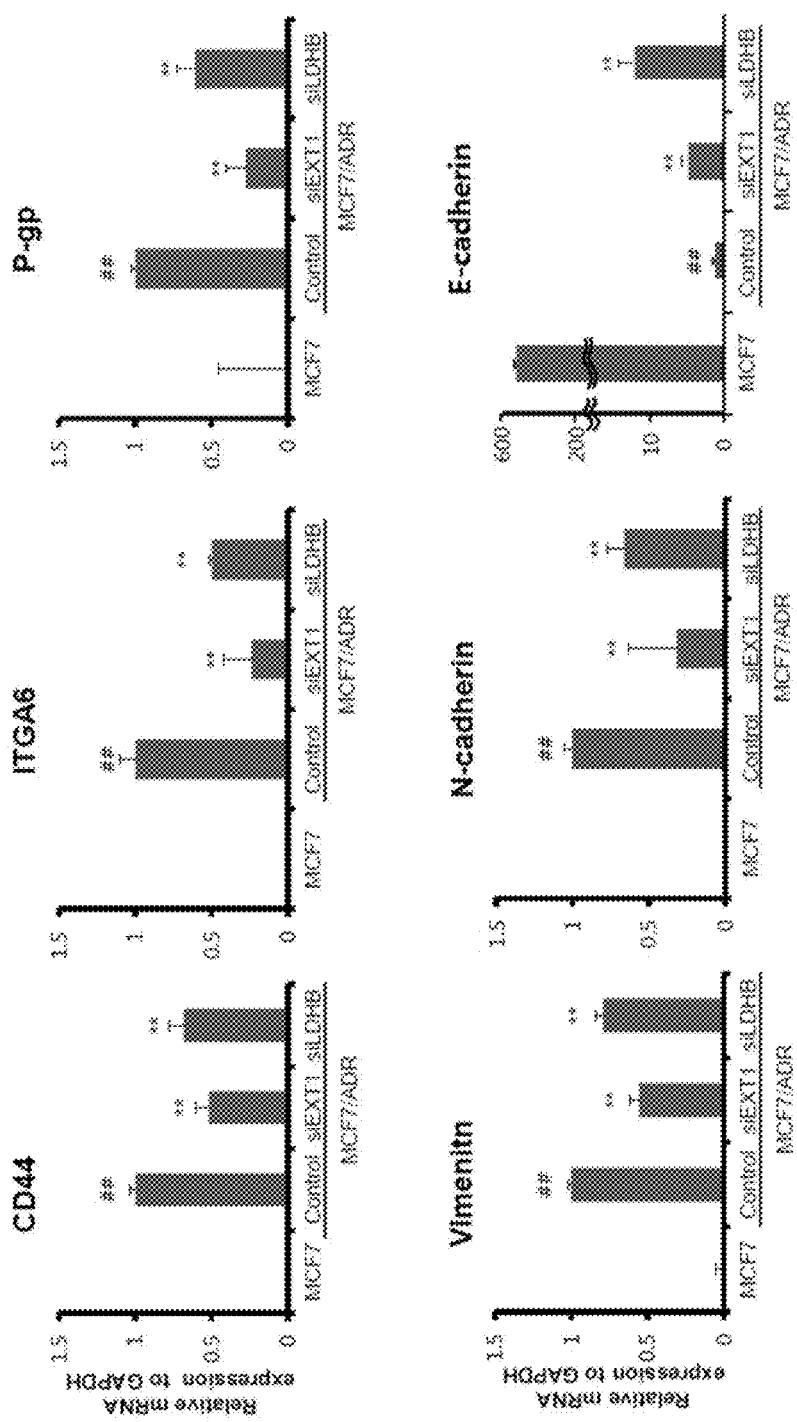
FIG. 8A is a diagram showing decreased mRNA expression levels of cancer stem cell markers (CD44, and Integrin-α6 (ITGA6)), a resistance marker (P-gp), and EMT markers (Vimentin, N-cadherin, and E-cadherin) after each of the EXT1 and LDHB genes is silenced with siRNA in the drug-resistant MCF7/ADR cells.

As a result, it was revealed that the stem cell markers (CD44, and Integrin-α6 (ITGA6)), the resistance marker (P-gp), and the EMT markers (Vimentin, N-cadherin, E-cadherin) were expressed at an increased level in the MCF7/ADR cells compared to the MCF7 cells, as shown in FIG. 8A. Also, it was confirmed that the expression of the markers was reduced in the MCF7/ADR cells when the EXT1 and LDHB genes were silenced with siRNA.

Figure 8B:
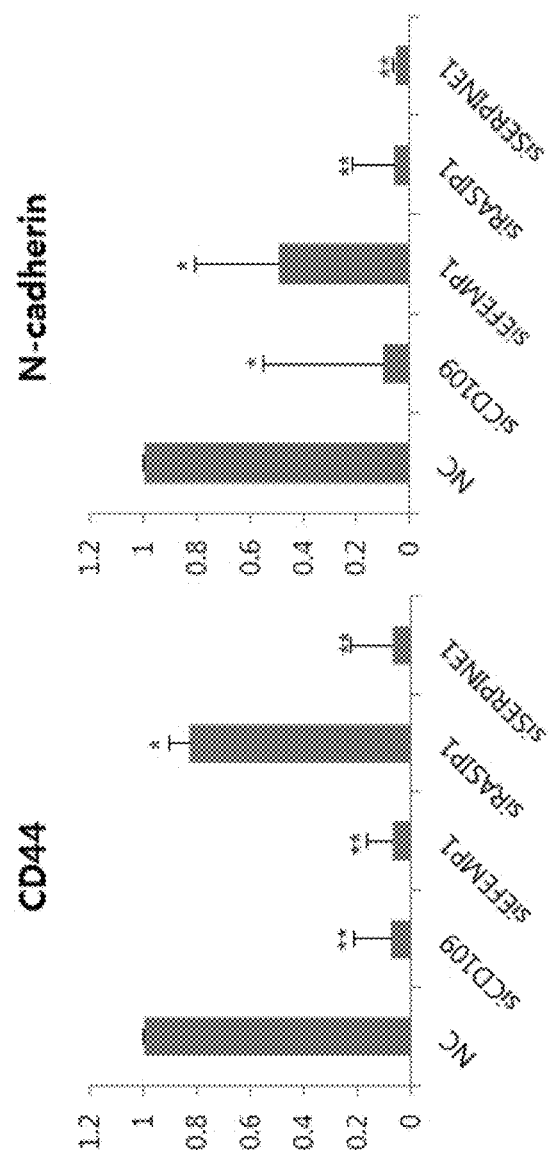
FIG. 8B is a diagram showing decreased mRNA expression levels of cancer stem cell marker (CD44) and EMT marker (N-cadherin) after each of the CD 109, EFEMP2, RASIP1 and SERPINE1 genes is silenced with siRNA in the drug-resistant MCF7/ADR cells.

Further, it was confirmed that the expression of the markers was reduced in the MCF7/ADR cells when the CD109, EFEMP2, RASIP1 and SERPINE1 genes were silenced with siRNA, as shown in FIG. 8B.

These results suggested that the EXT1, LDHB, CD109, EFEMP2, RASIP1 and SERPINE1 genes were regulators of the aggressive phenotype of cancer.

5-3. CD44+/CD24− and ALDEFLOUR Assay

Since the MCF7/ADR cell had a wider range of CSC characteristics, the EXT1 and LDHB genes were knocked down, and subjected to a CD44+/CD24− assay and an ALDEFLOUR assay so as to examine whether the genes regulated the cancer stem cell characteristics.

Figure 9A:
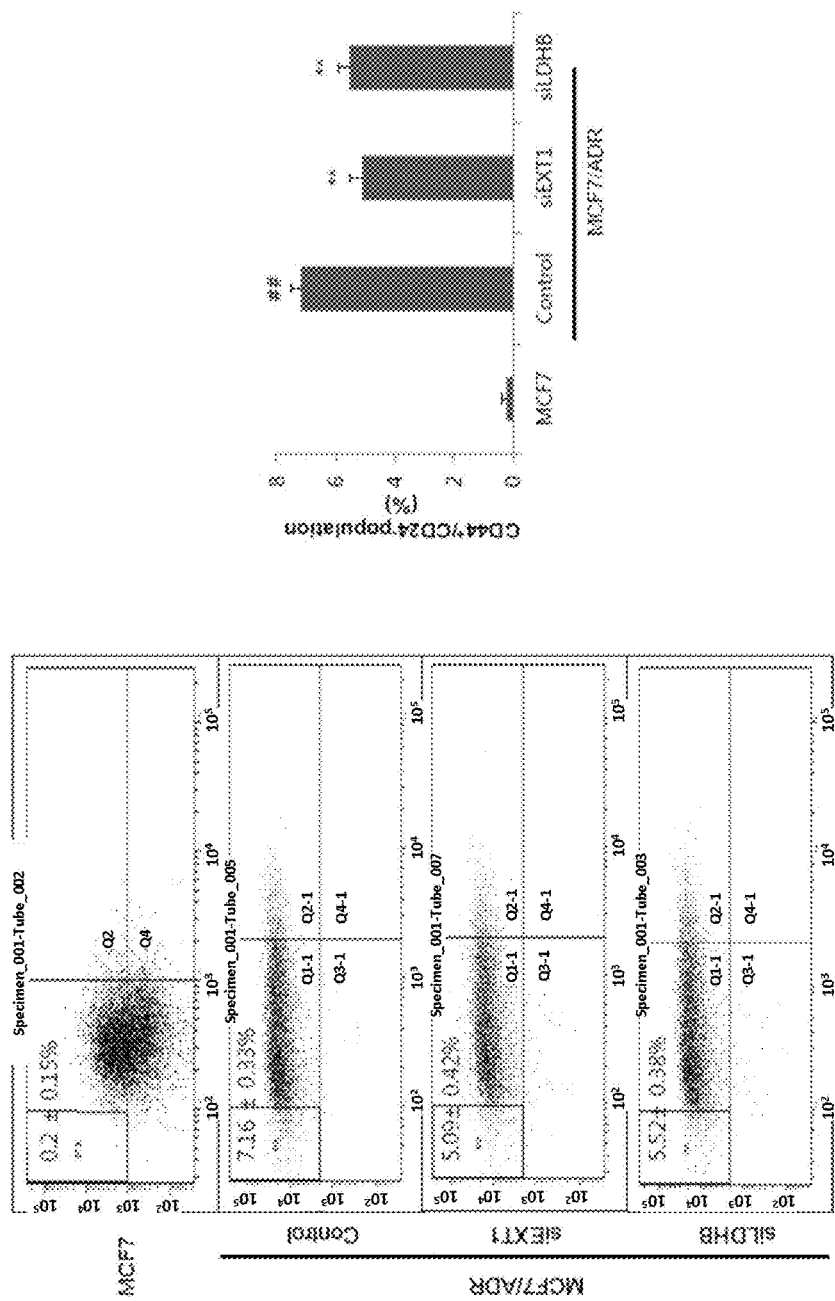
FIG. 9A is a diagram showing the results obtained by determining a decrease in CD44+/CD24− populations after each of the EXT1 and LDHB genes is silenced with siRNA in the drug-resistant MCF7/ADR cells.
Figure 9B:
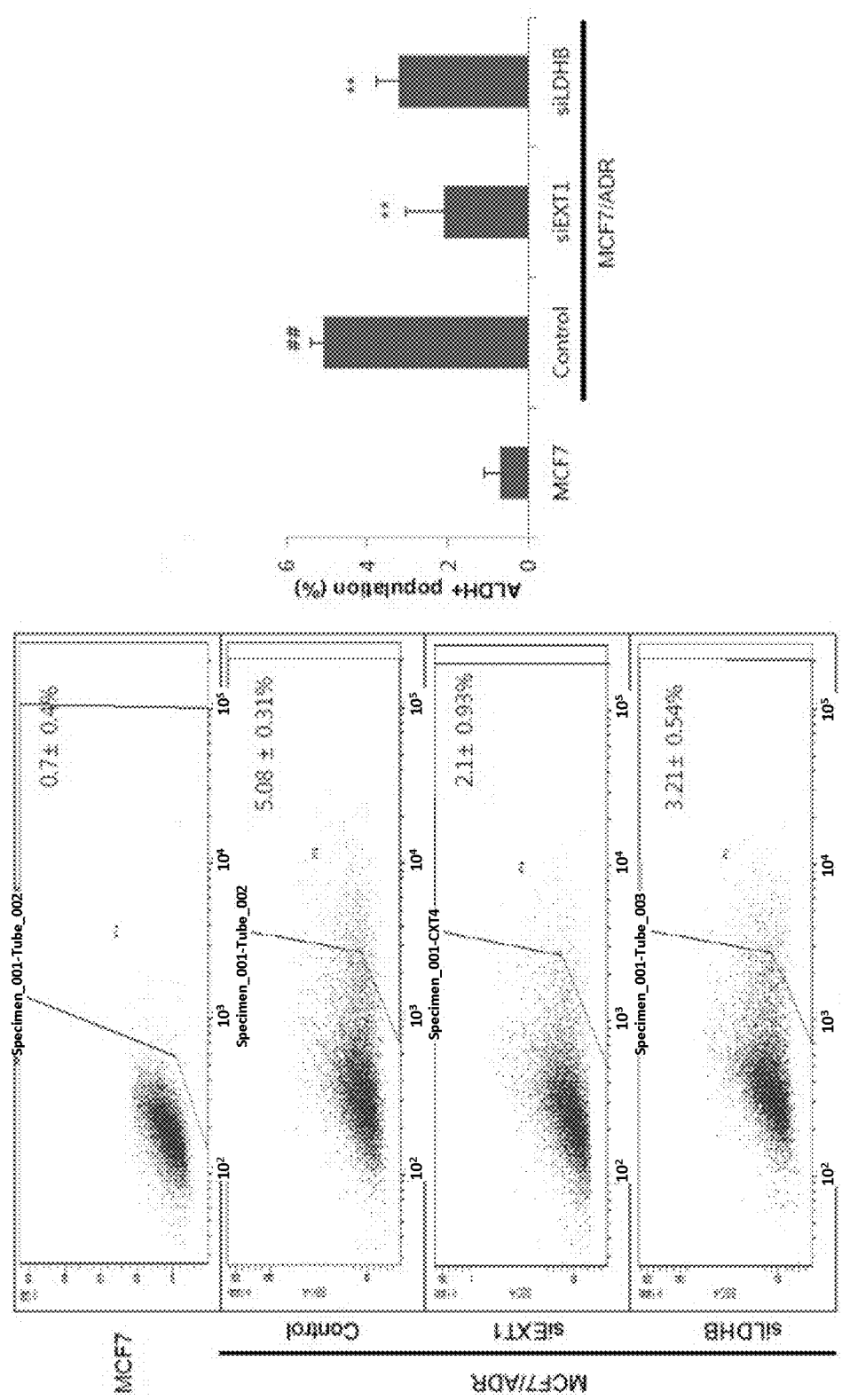
FIG. 9B is a diagram showing the results obtained by determining a decrease in ALDH+ populations after the silencing of the EXT1 and LDHB genes.

That is, the MCF7/ADR cells were transfected, and silenced with siRNAs against the EXT1 and LDHB genes (Table 3). As a result, it was revealed that the CD44+/CD24− populations of the MCF7/ADR cells decreased by approximately 5.09% and 5.52%, respectively, as shown in FIG. 9A. Also, it was revealed that the ALDH+ populations of the MCF7/ADR cells decreased by approximately 2.1% and 3.21%, respectively, through the silencing of the EXT1 and LDHB genes, as shown in FIG. 9B.

5-4. Mammosphere Formation Assay

To determine whether the EXT1 and LDHB regulated the self-renewal capacity of CSCs in the MCF7/ADR cells, a mammosphere formation assay was performed.

Figure 10:
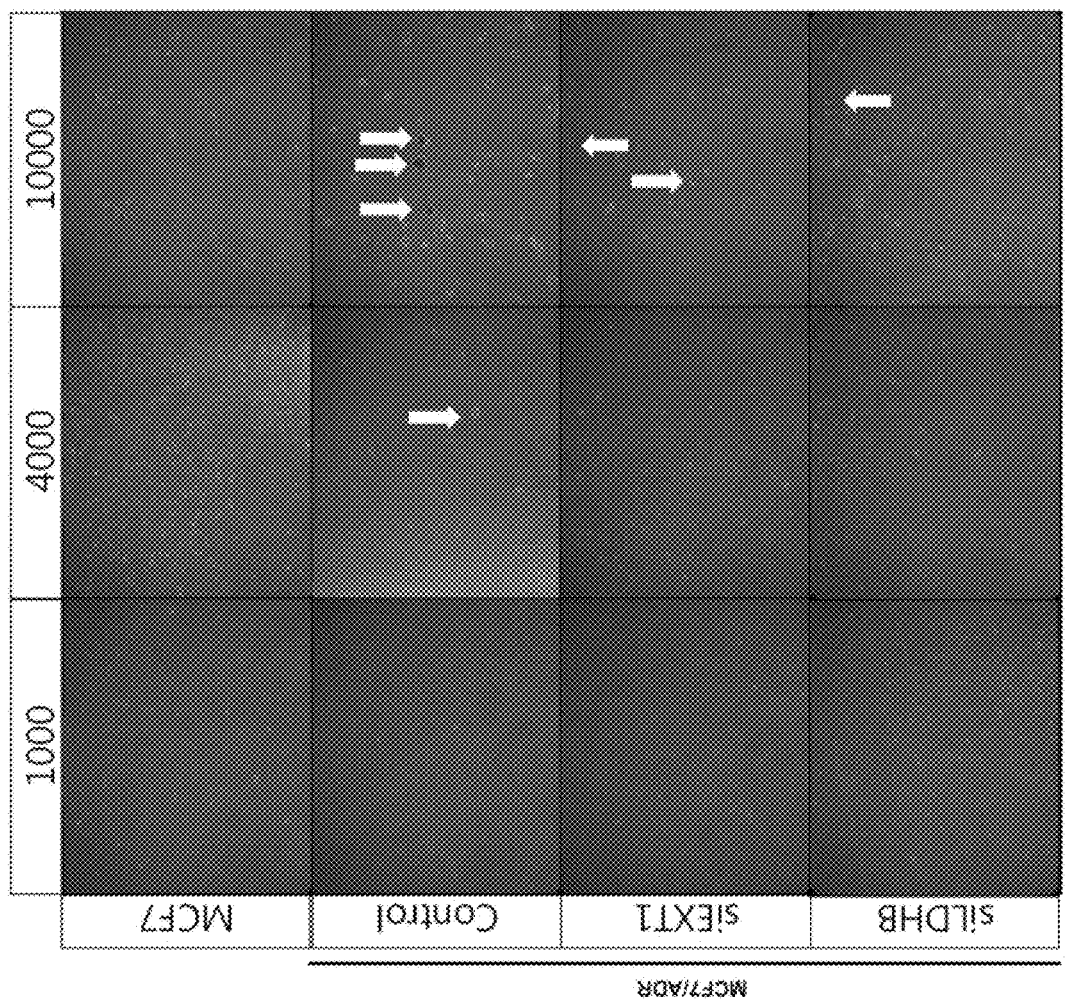
FIG. 10 is a diagram showing the results obtained by determining decreases in the number and size of mammospheres after each of the EXT1 and LDHB genes is silenced with siRNA in the drug-resistant MCF7/ADR cells.

As a result, it could be seen that the number and size of the mammospheres of the MCF7/ADR cells were significantly reduced, compared to the control, when the EXT1 or LDHB gene was silenced with siRNA (Table 3), as shown in FIG. 10.

These results indicated that the cancer stem cell characteristics were able to be degraded by inhibiting the expression of the EXT1 or LDHB gene.

EXAMPLE 6

PI3K-β-Catenin Signaling Pathway

Wnt signaling is a major pathway for maintaining stemness, and β-catenin is a particularly important regulator. Also, since the PI3K-Akt signaling pathway is known from previous research to regulate a Wnt-β-catenin signaling pathway, it was determined how the EXT1 and LDHB genes regulated the stemness, and whether the EXT1 and LDHB genes were associated with the pathways.

The MCF7/ADR cells activate Wnt signaling, and inactivate PI3K-Akt signaling since the MCF7/ADR cells include a higher number of cancer stem cells than the MCF7 cells.

Figure 11:
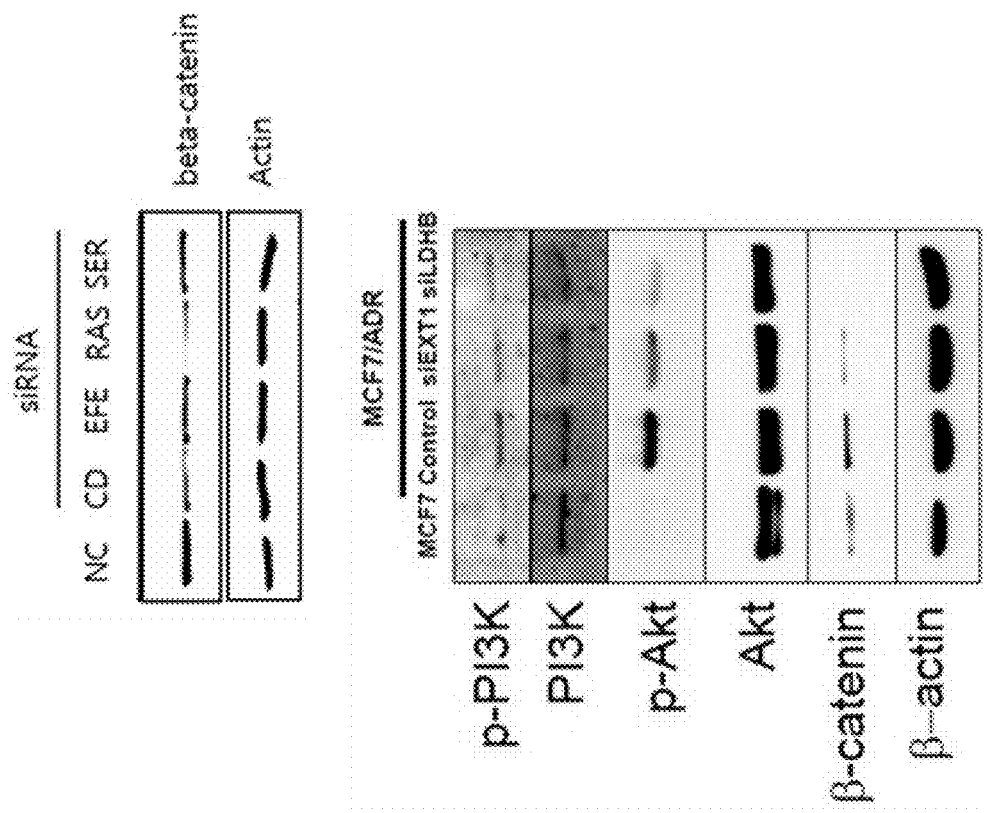
FIG. 11 is an image showing the results obtained by determining changes in expression of factors taking part in a PI3K-β-catenin signaling pathway after each of the EXT1, LDHB, CD109, EFEMP2, RASIP1 and SERPINE1 genes is silenced with siRNA in the drug-resistant MCF7/ADR cells.

Therefore, it was confirmed that, when the MCF7/ADR cells were treated with siRNAs against the EXT1, LDHB, CD109, EFEMP2, RASIP1 and SERPINE1 genes (Table 3), the expression of β-catenin decreased, and the expression of phosphorylated PI3K (p-PI3K) in an active form of PI3K, and phosphorylated Akt (p-Akt) in an active form of Akt increased (see FIG. 11).

Based on the results as described above, it could be seen that EXT1, LDHB, CD109, EFEMP2, RASIP1 and SERPINE1 regulated CSC by means of the PI3K-β-catenin signaling pathway.

It will be apparent to those skilled in the art that various modifications can be made to the above-described exemplary embodiments of the present invention without departing from the scope of the invention. Thus, it is intended that the present invention cover all such modifications provided they come within the scope of the appended claims and their equivalents.

According to the present invention, the pharmaceutical composition including the EXT1, LDHB, CD109, EFEMP2, RASIP1 or SERPINE1 gene expression inhibitor as an active ingredient targets therapeutic activities against cancer stem cells important for resistance, metastasis and recurrence of breast cancer, and thus can be useful in fundamentally treating, preventing or alleviating cancer such as breast cancer by directly inhibiting expression of EXT1, LDHB, CD109, EFEMP2, RASIP1 or SERPINE1 which are very important for growth of cancer stem cells.

What is claimed is:

1. A method for inhibiting growth of breast cancer stem cells, comprising administering a siRNA complementarily binding to EXT1 to the cells.

2. The method of claim 1, wherein the siRNA complementarily binding to the EXT1 gene has a sense sequence set forth in SEQ ID NO: 1, and an anti-sense sequence set forth in SEQ ID NO: 2.

* * * * *

```
                          SEQUENCE LISTING

<160> NUMBER OF SEQ ID NOS: 26

<210> SEQ ID NO 1
<211> LENGTH: 18
<212> TYPE: RNA
<213> ORGANISM: Artificial Sequence
<220> FEATURE:
<223> OTHER INFORMATION: Chemically synthesized

<400> SEQUENCE: 1
cacuucugga uaacucua                                                         18

<210> SEQ ID NO 2
<211> LENGTH: 19
<212> TYPE: RNA
<213> ORGANISM: Artificial Sequence
<220> FEATURE:
<223> OTHER INFORMATION: Chemically synthesized

<400> SEQUENCE: 2
uagaguuauc ccagaagug                                                        19

<210> SEQ ID NO 3
<211> LENGTH: 19
<212> TYPE: RNA
<213> ORGANISM: Artificial Sequence
<220> FEATURE:
<223> OTHER INFORMATION: Chemically synthesized

<400> SEQUENCE: 3
gauucauccc gugucaaca                                                        19

<210> SEQ ID NO 4
<211> LENGTH: 19
<212> TYPE: RNA
<213> ORGANISM: Artificial Sequence
<220> FEATURE:
<223> OTHER INFORMATION: Chemically synthesized

<400> SEQUENCE: 4
uguugacacg ggaugaauc                                                        19

<210> SEQ ID NO 5
<211> LENGTH: 19
<212> TYPE: RNA
<213> ORGANISM: Artificial Sequence
<220> FEATURE:
<223> OTHER INFORMATION: Chemically synthesized

<400> SEQUENCE: 5
gaguacugga gcggaucua                                                        19
```

<210> SEQ ID NO 6
<211> LENGTH: 18
<212> TYPE: RNA
<213> ORGANISM: Artificial Sequence
<220> FEATURE:
<223> OTHER INFORMATION: Chemically synthesized

<400> SEQUENCE: 6
uagauccguc caguacuc                                                 18

<210> SEQ ID NO 7
<211> LENGTH: 19
<212> TYPE: RNA
<213> ORGANISM: Artificial Sequence
<220> FEATURE:
<223> OTHER INFORMATION: Chemically synthesized

<400> SEQUENCE: 7
cccaaaccug ugucaacuu                                                19

<210> SEQ ID NO 8
<211> LENGTH: 19
<212> TYPE: RNA
<213> ORGANISM: Artificial Sequence
<220> FEATURE:
<223> OTHER INFORMATION: Chemically synthesized

<400> SEQUENCE: 8
aaguugacac agguuuggg                                                19

<210> SEQ ID NO 9
<211> LENGTH: 19
<212> TYPE: RNA
<213> ORGANISM: Artificial Sequence
<220> FEATURE:
<223> OTHER INFORMATION: Chemically synthesized

<400> SEQUENCE: 9
cuggauagua acccuuuca                                                19

<210> SEQ ID NO 10
<211> LENGTH: 19
<212> TYPE: RNA
<213> ORGANISM: Artificial Sequence
<220> FEATURE:
<223> OTHER INFORMATION: Chemically synthesized

<400> SEQUENCE: 10
ugaaaggguu acuauccag                                                19

<210> SEQ ID NO 11
<211> LENGTH: 19
<212> TYPE: RNA
<213> ORGANISM: Artificial Sequence
<220> FEATURE:
<223> OTHER INFORMATION: Chemically synthesized

<400> SEQUENCE: 11
cacacaaaag guaugauca                                                19

<210> SEQ ID NO 12
<211> LENGTH: 19
<212> TYPE: RNA
<213> ORGANISM: Artificial Sequence
<220> FEATURE:
<223> OTHER INFORMATION: Chemically synthesized -continued

```
<400> SEQUENCE: 12
ugaucauacc uuuugugug                                                    19

<210> SEQ ID NO 13
<211> LENGTH: 21
<212> TYPE: DNA
<213> ORGANISM: Artificial Sequence
<220> FEATURE:
<223> OTHER INFORMATION: Chemically synthesized

<400> SEQUENCE: 13
tgggaagatc gctactgaag c                                                 21

<210> SEQ ID NO 14
<211> LENGTH: 26
<212> TYPE: DNA
<213> ORGANISM: Artificial Sequence
<220> FEATURE:
<223> OTHER INFORMATION: Chemically synthesized

<400> SEQUENCE: 14
tttcctcaaa gagtttctgt atggta                                            26

<210> SEQ ID NO 15
<211> LENGTH: 20
<212> TYPE: DNA
<213> ORGANISM: Artificial Sequence
<220> FEATURE:
<223> OTHER INFORMATION: Chemically synthesized

<400> SEQUENCE: 15
acttcatggt cccagtgctc                                                   20

<210> SEQ ID NO 16
<211> LENGTH: 20
<212> TYPE: DNA
<213> ORGANISM: Artificial Sequence
<220> FEATURE:
<223> OTHER INFORMATION: Chemically synthesized

<400> SEQUENCE: 16
aaatccgggt ttctttcaca                                                   20

<210> SEQ ID NO 17
<211> LENGTH: 24
<212> TYPE: DNA
<213> ORGANISM: Artificial Sequence
<220> FEATURE:
<223> OTHER INFORMATION: Chemically synthesized

<400> SEQUENCE: 17
tgtccaaatc gatgtggatg tttc                                              24

<210> SEQ ID NO 18
<211> LENGTH: 23
<212> TYPE: DNA
<213> ORGANISM: Artificial Sequence
<220> FEATURE:
<223> OTHER INFORMATION: Chemically synthesized

<400> SEQUENCE: 18
ttgtaccatt cttctgcctc ctg                                               23

<210> SEQ ID NO 19
```

```
<211> LENGTH: 20
<212> TYPE: DNA
<213> ORGANISM: Artificial Sequence
<220> FEATURE:
<223> OTHER INFORMATION: Chemically synthesized

<400> SEQUENCE: 19
acagtggcca cctacaaagg                                                   20

<210> SEQ ID NO 20
<211> LENGTH: 20
<212> TYPE: DNA
<213> ORGANISM: Artificial Sequence
<220> FEATURE:
<223> OTHER INFORMATION: Chemically synthesized

<400> SEQUENCE: 20
ccgagatggg gttgataatg                                                   20

<210> SEQ ID NO 21
<211> LENGTH: 20
<212> TYPE: DNA
<213> ORGANISM: Artificial Sequence
<220> FEATURE:
<223> OTHER INFORMATION: Chemically synthesized

<400> SEQUENCE: 21
gagagcggtg gtcaaagagc                                                   20

<210> SEQ ID NO 22
<211> LENGTH: 20
<212> TYPE: DNA
<213> ORGANISM: Artificial Sequence
<220> FEATURE:
<223> OTHER INFORMATION: Chemically synthesized

<400> SEQUENCE: 22
gaggagttca gggagctcag                                                   20

<210> SEQ ID NO 23
<211> LENGTH: 20
<212> TYPE: DNA
<213> ORGANISM: Artificial Sequence
<220> FEATURE:
<223> OTHER INFORMATION: Chemically synthesized

<400> SEQUENCE: 23
aatcccatca ccatcttcca                                                   20

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized

<400> SEQUENCE: 24
tggactccac gacgtactca                                                   20

<210> SEQ ID NO 25
<211> LENGTH: 20
<212> TYPE: DNA
<213> ORGANISM: Artificial Sequence
<220> FEATURE:
<223> OTHER INFORMATION: Chemically synthesized

<400> SEQUENCE: 25
```
gtgctgatgg caaccaactg                                              20

<210> SEQ ID NO 26
<211> LENGTH: 20
<212> TYPE: DNA
<213> ORGANISM: Artificial Sequence
<220> FEATURE:
<223> OTHER INFORMATION: Chemically synthesized

<400> SEQUENCE: 26
ctcaaaaggc gatcccacct                                              20